US00PP36685P2

(12) United States Plant Patent
Randag

(10) Patent No.: US PP36,685 P2
(45) Date of Patent: May 13, 2025

(54) CALLA LILY PLANT NAMED 'Dozanwhamb'

(50) Latin Name: *Zantedeschia sprengeri*
Varietal Denomination: Dozanwhamb

(71) Applicant: Dümmen Group B.V., De Lier (NL)

(72) Inventor: Cecilius Jan-Jochem Randag, Koedijk (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 18/815,996

(22) Filed: Aug. 27, 2024

(51) Int. Cl.
*A01H 5/02* (2018.01)
*A01H 6/10* (2018.01)

(52) U.S. Cl.
USPC ..... Plt./490

(58) Field of Classification Search
USPC ..... Plt./490
CPC ..... A01H 5/02; A01H 5/00; A01H 6/10
See application file for complete search history.

*Primary Examiner* — June Hwu
(74) *Attorney, Agent, or Firm* — The Webb Law Firm

(57) ABSTRACT

'Dozanwhamb' is a new variety of calla lily plant having white spathes without a throat spot that produces approximately 11 inflorescences per 20-22 cm diameter tuber.

2 Drawing Sheets

Botanical classification: *Zantedeschia sprengeri*.
Varietal denomination: 'DOZANWHAMB'.

BACKGROUND OF THE INVENTION

The present invention comprises a new and distinct variety of calla lily, botanically known as *Zantedeschia sprengeri*, and hereinafter referred to by the varietal name 'Dozanwhamb'. 'Dozanwhamb' is a product of a planned breeding program, which had the objective of creating *Zantedeschia* varieties for pot flower production in a wide range of colors and flower shapes. The new variety is the result of the crossing of *Zantedeschia sprengeri* variety having an internal breeder reference of ZS10-K0239 (female parent, unpatented) with *Zantedeschia sprengeri* variety having an internal breeder reference of ZS11-K0207 (male parent, unpatented). 'Dozanwhamb' was selected in May of 2016 by the inventor in 't Zand, The Netherlands as one flowering plant within the progeny of the stated cross.

The first act of asexual reproduction of 'Dozanwhamb' by tissue culture was performed by the inventor in August of 2016 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction. The present invention has not been evaluated under all possible environmental conditions. The phenotype may vary with variations in environment without a change in the genotype of the plant.

The following observations, measurements and comparisons describe plants at from 1 to 5 months from planting in a 19 cm pot in 't Zand, The Netherlands under greenhouse conditions, which approximate those generally used in horticultural practice. Color references are made to The 2001 R.H.S. Colour Chart of The Royal Horticultural Society of London, 4$^{th}$ Edition, except where general color terms of ordinary significance are used.

The following traits have been repeatedly observed and determined to be basic characteristics of 'Dozanwhamb' which, in combination, distinguish this calla lily as a new and distinct cultivar:

1. White colored spathes without a throat spot;
2. Lanceolate-shaped leaves;
3. Low to medium amount of leaf maculation; and
4. A yellow-green young shoot color with a slight blush of red present.

The new variety is similar to its female parent in having a white spathe color without a throat spot. However, 'Dozanwhamb' is shorter in overall plant height than its female parent. Further, its female parent has oval-shaped leaves with medium to high maculation present. The new variety is similar to its male parent in having a white spathe color without a throat spot, as well as in leaf shape and maculation presence. However, the new variety exhibits a lower number of sprouts and is taller than its male parent.

When compared to calla lily plant named 'White Art' (unpatented), the varieties are similar in spathe, leaf, and peduncle colors. However, the new variety has fewer leaf maculations, less red coloration on young shoots, and a longer spathe than 'White Art'.

BRIEF DESCRIPTION OF THE DRAWINGS

The accompanying photographic drawings illustrate the new variety taken at approximately 3 months of age, with the colors being as nearly true as is possible with color illustrations of this type.

DESCRIPTION OF THE NEW PLANT

Figure 1:
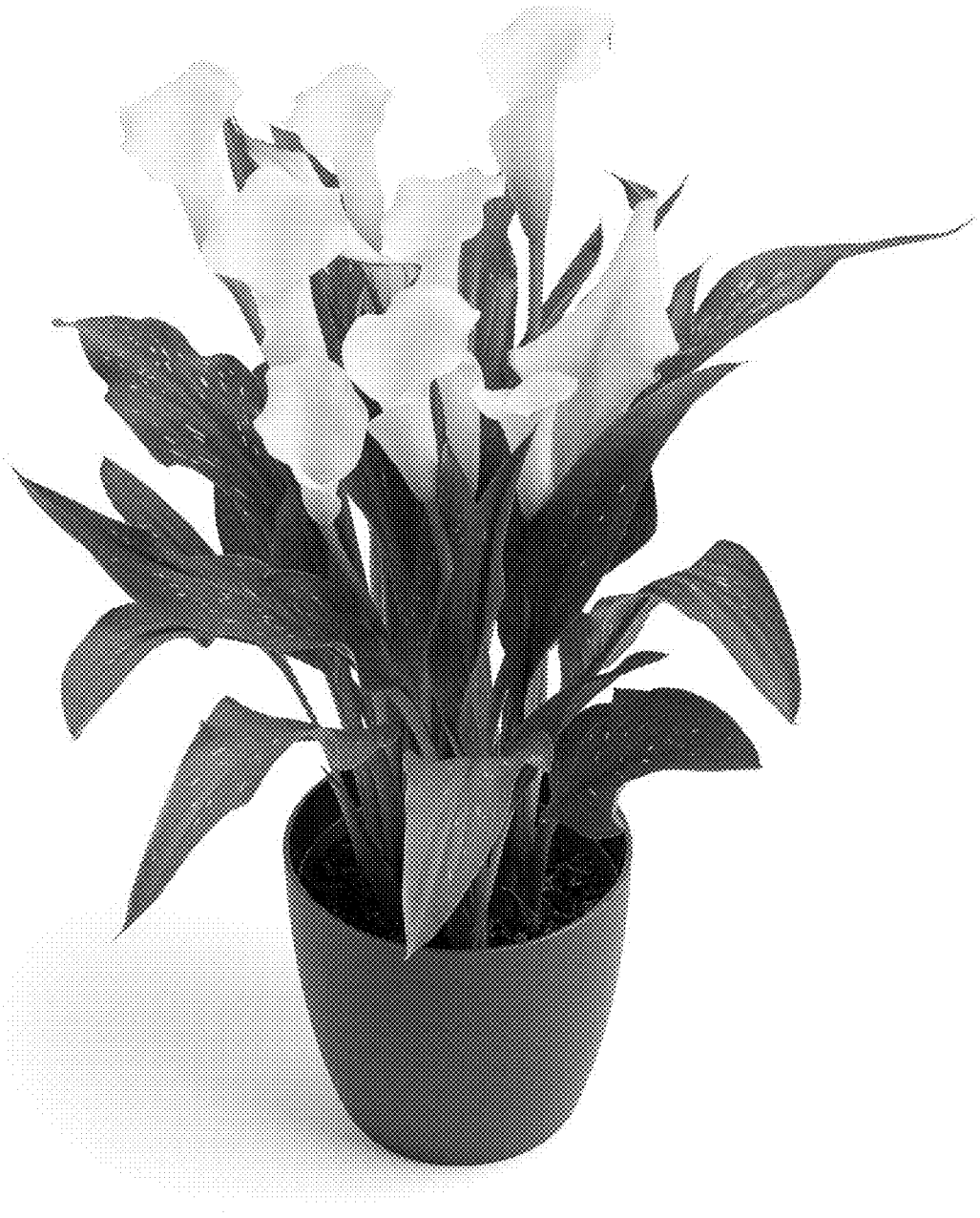
FIG. 1 illustrates a flowering plant of the new variety.
Figure 2:
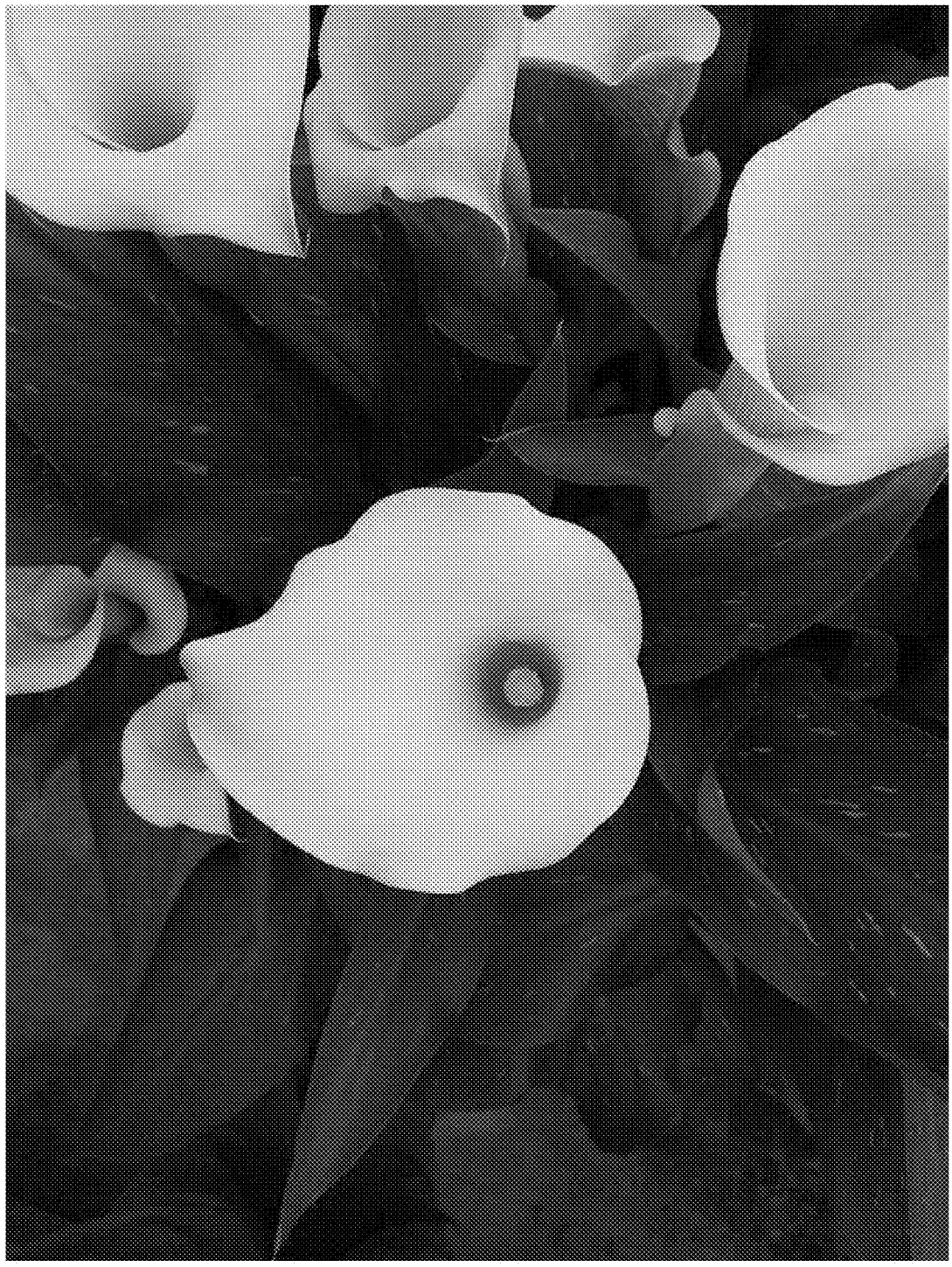
FIG. 2 illustrates a close-up view of the spathes of the new variety.

Type: Deciduous.
Use: Cut flowers and as an ornamental potted plant.

Size:

*Height of the leaf canopy above the soil.*—73-85 cm (78 cm average).

*Height of top of inflorescences above the soil.*—57-80 cm (74 cm average).

*Diameter.*—47-60 cm leaf canopy (54.2 cm average) for a 20-22 cm diameter tuber.

Form: Semi-spreading.

Number of inflorescences per tuber:

*Size approximately* 20-22 *cm in diameter.*—Average of 11.4 inflorescences.

Branches:

*Number.*—Average of 14 for a 20-22 cm diameter tuber.

*Color.*—Yellow-Green Group RHS 144A.

*Young shoot color.*—Yellow-Green Group RHS 150B to 150C with a slight blush of Red Group RHS 46A present.

Leaves:

*Size.*—Width: 7.5-11.5 cm (9.2 cm average). Length: 23-35 cm (29.4 cm average).

*Number per plant.*—23-36 (31.6 average) for a 20-22 cm diameter tuber.

*Leaf blade lobes.*—Absent.

*Shape.*—Lanceolate.

*Apex.*—Caudate to apiculate.

*Base.*—Attenuate.

*Margin.*—Entire.

*Color.*—Upper surface: Green Group RHS 137A to 137B, with White Group RHS 155C maculations present. Lower surface: Green Group RHS 137A to 137B, with White Group RHS 155C maculations present.

*Veins.*—Configuration: Pinnate. Color: Yellow-Green Group RHS 144A.

*Surface texture.*—Leathery (both surfaces).

*Lobes.*—Not present.

*Petiole.*—Length: 32-44 cm (38.9 cm average). Diameter: 0.7-1.1 cm (1 cm average). Texture: Smooth. Shape: Cylindrical, with a U-shaped groove on the upper leaf side. Color: Both surfaces are Yellow-Green Group RHS 144A.

Roots:

*Color.*—White Group RHS 155C.

*Branching description.*—Fibrous root system, main roots emerge from the top of the tuber and will develop a small number of lateral roots.

Spathe:

*Size.*—Length (measured from base to tip): 10-14 cm (12.9 cm average). Width: 5-7 cm (5.8 cm average).

*Color.*—Throat spot: Absent, remains as White Group RHS 155C. Upper surface: White Group RHS 155C. Lower surface: White Group RHS 155C and Yellow-Green Group RHS 145C. Vein: Yellow-Green Group RHS 144B to 144C.

*Shape.*—Funnel.

*Apex.*—Apiculate to acuminate.

*Base.*—Amplexicaul.

*Margin.*—Entire.

*Fragrance.*—None.

Spadix:

*Shape.*—Cylinder.

*Apex shape.*—Obtuse.

*Apex color.*—Yellow Group RHS 5C.

*Size.*—Length: 3.7-4.7 cm (4.1 cm average). Diameter: 0.7-0.9 cm (0.8 cm average).

*Color.*—Male region: Yellow Group RHS 9C. Female region: Green-Yellow Group RHS 1D.

*Position relative to spathe.*—Upright.

*Female flower.*—Number: 16 to 41 (26.3 average). Shape: Round. Height: 2-3 mm (immature). Diameter: 2-4 mm (immature).

*Male flower.*—Number: 350-550. Shape: Round. Height: About 1 mm. Diameter: About 1 mm.

Peduncle:

*Size.*—Length: 54-61 cm (57.5 cm average). Diameter: 0.7-1.0 cm (0.9 cm average).

*Strength.*—Moderate.

*Color.*—Yellow-Green Group RHS 144B to 144C.

*Texture.*—Smooth.

Reproductive organs:

*Location of female organs.*—Base of the spadix.

*Location of male organs.*—Apex of the spadix.

*Perianth.*—Inconspicuous.

*Stamens.*—Number: Between 350-550. Pollen amount: Abundant; too much to quantify. Color: Yellow Group RHS 9C.

*Anther.*—Shape: Round. Length: About 1 mm. Color: Yellow Group RHS 9C.

*Filament.*—Length: Less than 1 mm. Color: Yellow Group RHS 9C.

*Pistils.*—Number: 16 to 41 (26.3 average). Length beyond perianth: 2-3 mm.

*Stigma.*—Shape: Round. Length: Less than 1 mm. Diamter: About 1 mm.

*Style.*—Length: Less than 1 mm. Color: Green-Yellow Group RHS 1D to Yellow Group RHS 9C.

*Ovaries.*—Texture: Smooth, with some ridges around the edges. Length: Between 6-14 mm. Width: Between 5-18 mm. Color: The immature color is Green-Yellow Group RHS 1D and the mature color is Yellow-Green Group RHS 145A to 145C.

Seeds:

*Length.*—5-9 mm (fresh).

*Width.*—4-7 mm (fresh).

*Color.*—Yellow-Green Group RHS 145B to 145C (fresh).

*Amount.*—Average of 71.5 per flower.

Disease resistance: No unusual susceptibility/resistance to diseases noticed to date.

Pest resistance: No unusual susceptibility/resistance to pests noticed to date.

Heat/cold tolerance: Not tested to date.

Hardiness: Not tested to date.

Flowering: In general, the time from indoor and outdoor planting to first flowering takes about 70 days in The Netherlands.

Lastingness: About two weeks on the plant.

I claim:

1. A new and distinct variety of calla lily plant named 'Dozanwhamb', as is herein illustrated and described.

* * * * *